(12) United States Patent
Morimoto et al.

(10) Patent No.: US 12,279,938 B2
(45) Date of Patent: *Apr. 22, 2025

(54) WEARABLE ARTICLE HAVING ELASTIC BELT

(71) Applicant: The Procter & Gamble Company, Cincinnati, OH (US)

(72) Inventors: Koichi Morimoto, Beijing (CN); Hui Liu, Beijing (CN)

(73) Assignee: The Procter & Gamble Company, Cincinnati, OH (US)

(*) Notice: Subject to any disclaimer, the term of this patent is extended or adjusted under 35 U.S.C. 154(b) by 146 days.

This patent is subject to a terminal disclaimer.

(21) Appl. No.: 18/110,966

(22) Filed: Feb. 17, 2023

(65) Prior Publication Data

US 2023/0190541 A1 Jun. 22, 2023

Related U.S. Application Data

(63) Continuation of application No. 16/550,401, filed on Aug. 26, 2019, now Pat. No. 11,622,894, which is a
(Continued)

(51) Int. Cl.
*A61F 13/496* (2006.01)
*A61F 13/49* (2006.01)

(52) U.S. Cl.
CPC .... *A61F 13/49012* (2013.01); *A61F 13/4902* (2013.01); *A61F 13/4963* (2013.01);
(Continued)

(58) Field of Classification Search
CPC ............ A61F 13/4902; A61F 13/49011; A61F 13/49012; A61F 13/4906; A61F 13/49061; A61F 2013/49025; A61F 2013/49033
See application file for complete search history.

(56) References Cited

U.S. PATENT DOCUMENTS 7,901,393 B2  3/2011  Matsuda
8,298,205 B2  10/2012  Norrby
(Continued)

FOREIGN PATENT DOCUMENTS

CN    1784192 A    6/2006
CN  101106962 A    1/2008
(Continued)

OTHER PUBLICATIONS

"Polyethylene terephthalate" Retrieved From https://en.wikipedia.org/wiki/Polyethylene_terephthalate, 2022, 18 Pages.
(Continued)

*Primary Examiner* — Susan S Su
(74) *Attorney, Agent, or Firm* — Charles R. Matson; Richard L. Alexander

(57) ABSTRACT

Disclosed is a wearable article continuous in a longitudinal direction and a transverse direction comprising an elastic belt region, a crotch region, a waist opening and two leg openings; wherein the elastic belt region is a laminate comprising an inner sheet made of nonwoven fiber, and an outer sheet made of nonwoven fiber, and a plurality of elastic bodies configured to stretch the elastic belt region in the transverse direction, wherein the article has a Compression Work index of at least about 70 gfcm and a Stretch Circumference Force of less than about 6.5N according to the measurements herein.

11 Claims, 10 Drawing Sheets

Related U.S. Application Data continuation of application No. PCT/CN2017/074993, filed on Feb. 27, 2017.

(52) U.S. Cl.
CPC ............... *A61F 2013/49022* (2013.01); *A61F 2013/49034* (2013.01)

(56) References Cited

U.S. PATENT DOCUMENTS

| | | |
|---|---|---|
| 8,622,983 B2 | 1/2014 | Wilkes |
| 9,220,643 B2 | 12/2015 | Yamashita |
| 9,421,134 B2 | 8/2016 | Schlinz |
| 9,549,859 B2 | 1/2017 | Wilkes |
| 2004/0102757 A1 | 5/2004 | Olson |
| 2004/0243083 A1 | 12/2004 | Matsuda |
| 2006/0030831 A1 | 2/2006 | Matsuda |
| 2011/0160692 A1 | 6/2011 | Wilkes |
| 2013/0211363 A1 | 8/2013 | Lavon |
| 2014/0088542 A1 | 3/2014 | Wilkes |
| 2014/0332436 A1 | 11/2014 | Sasayama |
| 2016/0331600 A1 | 11/2016 | Polidori |
| 2017/0156945 A1 | 6/2017 | Hashimoto |
| 2017/0165128 A1 | 6/2017 | Morimoto |
| 2017/0189244 A1 | 7/2017 | Mueller |
| 2017/0335498 A1 | 11/2017 | Hansen |
| 2018/0168885 A1 | 6/2018 | Zink, II |
| 2019/0374402 A1 | 12/2019 | Morimoto et al. |

FOREIGN PATENT DOCUMENTS

| | | |
|---|---|---|
| CN | 203885725 U | 10/2014 |
| EP | 937793 A2 | 8/1997 |
| EP | 3326596 | 5/2018 |
| JP | 2004081365 A | 3/2004 |
| JP | 2005052186 A | 3/2005 |
| JP | 2007159943 A | 6/2007 |
| JP | 2009056142 A | 3/2009 |
| JP | 2012091054 A | 5/2012 |
| JP | 2013102885 A | 5/2013 |
| WO | 2016029566 A1 | 3/2016 |
| WO | 2016029655 A1 | 3/2016 |
| WO | 2016101197 A1 | 6/2016 |
| WO | 2016101198 A1 | 6/2016 |
| WO | 2016168997 A1 | 10/2016 |

OTHER PUBLICATIONS

PCT Search Report and Written Opinion for PCT/CN2017/074993 dated Nov. 30, 2017, 9 pages.

Supplemental International Search Report and Written Opinion for;PCT/CN2017 /074993 dated Mar. 6, 2019, 11 pages.

All Office Actions; U.S. Appl. No. 16/550,401, filed Aug. 26, 2019.

WEARABLE ARTICLE HAVING ELASTIC BELT

CROSS REFERENCE TO RELATED APPLICATION

This application is a continuation of U.S. application Ser. No. 16/550,401, filed on Aug. 26, 2019, which is a continuation, under 35 USC 120, of Application No. PCT/CN2017/074993, filed on Feb. 27, 2017, both of which are herein incorporated by reference.

FIELD OF THE INVENTION

The present invention relates to wearable articles having an elastic belt region having characteristic material properties and force profiles.

BACKGROUND OF THE INVENTION

Infants and other incontinent individuals wear absorbent articles such as diapers to receive and contain urine and other body exudates. Pull-on absorbent articles, or pant-type absorbent articles, are those which are donned by inserting the wearer's legs into the leg openings and sliding the article up into position about the lower torso. Pant-type absorbent articles have become popular for use on children who are able to walk and often who are toilet training, as well as for younger children who become more active in movement such that application of taped-type absorbent articles tends to be more difficult, and also for younger babies requiring a soft fit around the waist opening and leg openings.

Pant-type articles may take various structures wherein the circumference of the waist opening and vicinity thereof is made elastic enough to facilitate the wearer or the caregiver to expand the article and insert the wearer's legs into the leg openings for wearing the article. The region of the waist circumference and vicinity thereof is often referred to as the elastic belt. One type of structure for the pant-type article is the belt-type pant having a main body to cover the crotch region of the wearer and a separate elastic belt defining the waist opening and leg opening, such as described in PCT Publication WO 2006/17718A. Another type of structure for the pant-type articles is the uni-body pant configured such that the outer cover of the article completely covers the entirety of the garment-facing surface of the article, wherein the portion configured to stretch about the torso is considered the elastic belt region.

Whatever the structure of the pant-type article may be, the elastic belt region is the portion which is most touched and observed by the wearer or the caregiver upon use, and thus its properties most associated with the function and quality of the article. By function, what may be desired is easy stretch opening upon application and soft fit to the skin to avoid red markings during wear, while having enough force to prevent the article from sagging after loading. By quality, what may be desired is an undergarment kind of appearance, and pleasant tactile sense such as flexibility and cushiony touch.

Meanwhile, from a manufacturer's point of view, there is desire to provide a high quality absorbent article while controlling cost for making the article by selecting materials and assembling them in a manner that may provide the best user experience per cost of material.

Based on the foregoing, there is a need for a pant-type wearable article having improved tactile and aesthetic sense for the elastic belt region without compromise to ease of application, fit, comfort during wear, prevention of sagging, and prevention of leakage. There is further a need for providing such a wearable article in an economical manner

SUMMARY OF THE INVENTION

The present invention is directed to a wearable article continuous in a longitudinal direction and a transverse direction comprising an elastic belt region, a crotch region, a waist opening and two leg openings;
  wherein the elastic belt region is a laminate comprising an inner sheet made of nonwoven fiber, and an outer sheet made of nonwoven fiber, and a plurality of elastic bodies configured to stretch the elastic belt region in the transverse direction,
  wherein the article has a Compression Work index of at least about 70 gfcm and a Stretch Circumference Force of less than about 6.5N according to the measurements herein.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DEFINITIONS

Figure 1:
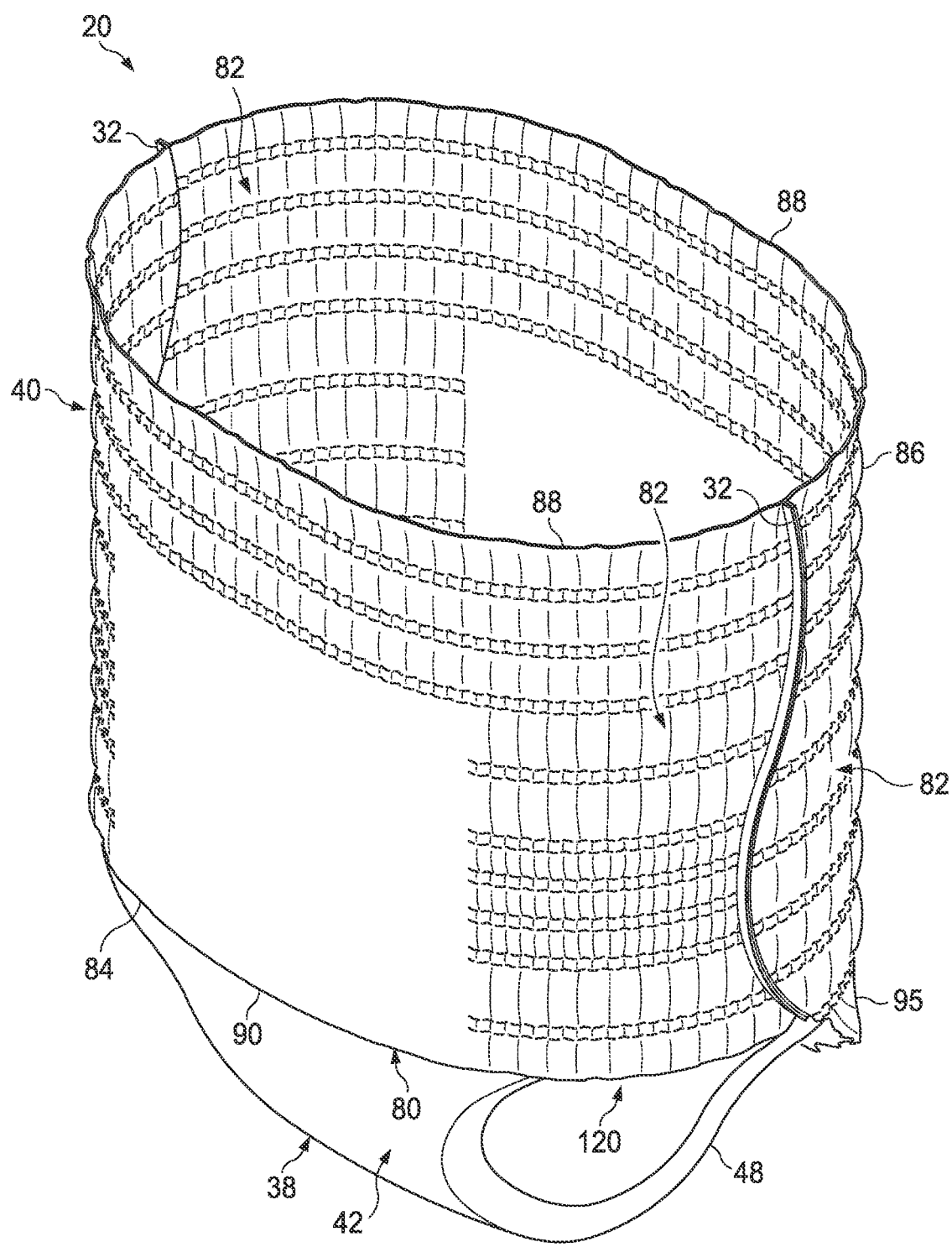
FIG. 1 is a perspective view of one embodiment of a wearable article of the present invention.

As used herein, the following terms shall have the meaning specified thereafter:

"Wearable article" refers to articles of wear which may be in the form of pants, taped diapers, incontinent briefs, feminine hygiene garments, and the like. The "wearable article" may be so configured to also absorb and contain various exudates such as urine, feces, and menses discharged from the body. The "wearable article" may serve as an outer cover adaptable to be joined with a separable disposable absorbent insert for providing absorbent and containment function, such as those disclosed in PCT publication WO 2011/087503A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants".

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Proximal" and "distal" refer respectively to the position closer or farther relative to the longitudinal center of the article.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable".

"Extendibility" and "extensible" mean that the width or length of the component in a relaxed state can be extended or increased.

"Elasticated" and "elasticized" mean that a component comprises at least a portion made of elastic material.

"Elongatable material", "extensible material", or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Artwork" refers to a visual presentation to the naked eye, which is provided by printing or otherwise, and having a color. Printing includes various methods and apparatus well known to those skilled in the art such as lithographic, screen printing, flexographic, and gravure ink jet printing techniques.

"Color" or "Colored" as referred to herein includes any primary color except color white, i.e., black, red, blue, violet, orange, yellow, green, and indigo as well as any declination thereof or mixture thereof. The color white is defined as those colors having a L* value of at least 94, an a* value equal to 0±2, and a b* value equal to 0±2 according to the CIE L* a* b* color system.

DETAILED DESCRIPTION OF THE INVENTION

Figure 2:
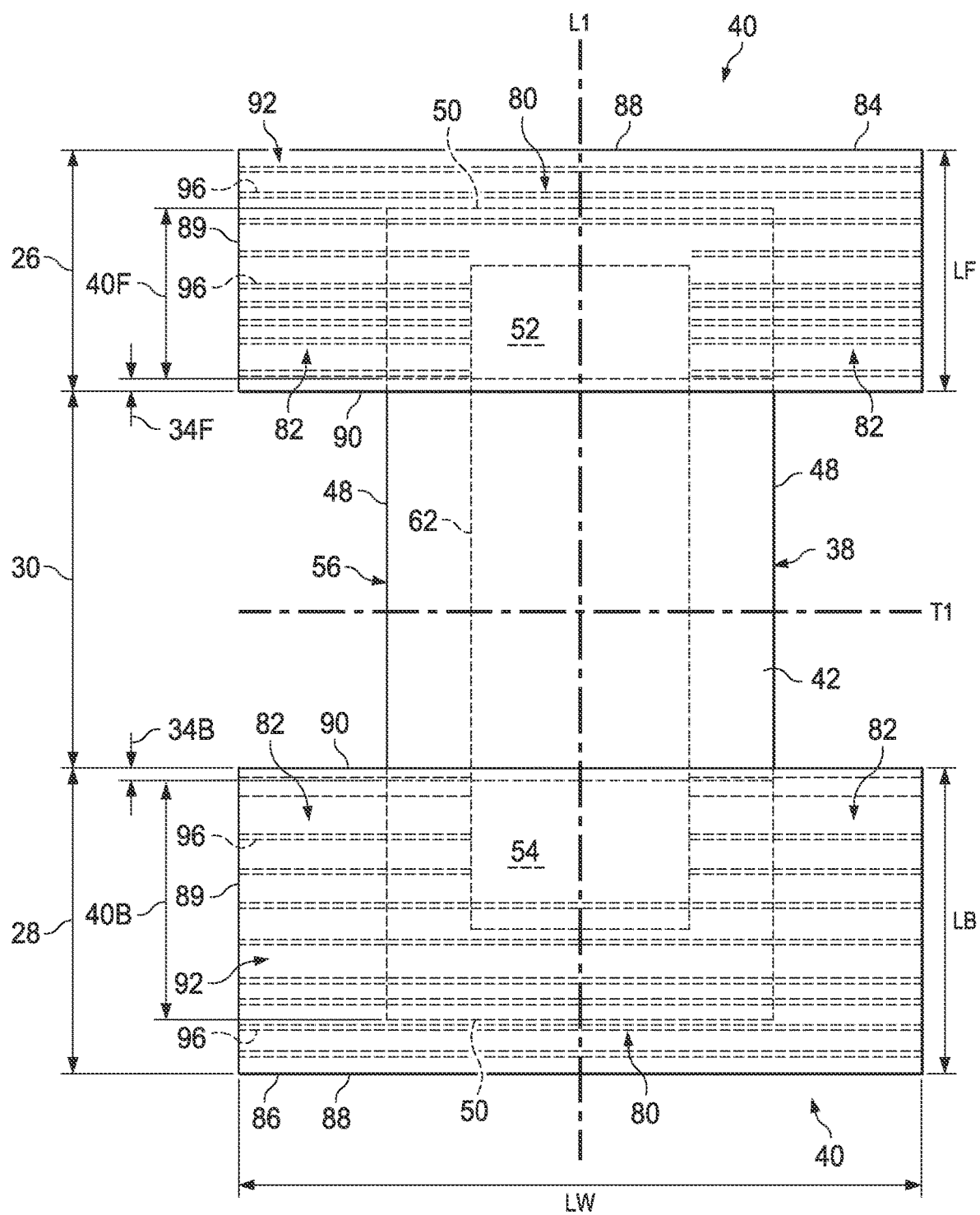
FIG. 2 is a schematic plan view of one embodiment of a wearable article of the present invention with the seams unjoined and removed, and in a flat uncontracted condition showing the garment facing surface.

FIG. 1 is a perspective view of an embodiment of the wearable article 20 of the present invention and FIG. 2 is a schematic plan view of the same article with the seams unjoined and in its flat uncontracted condition showing the garment-facing surface. The wearable article 20 has a longitudinal centerline L1 which also serves as the longitudinal axis, and a transverse centerline T1 which also serves as the transverse axis. The wearable article 20 has a body facing surface, a garment facing surface, a front region 26, a back region 28, a crotch region 30, and seams 32 which join the front region 26 and the back region 28 to form two leg openings and a waist opening. The wearable article 20 may be a belt-type pant comprising a central chassis 38 to cover the crotch region of the wearer, a front belt 84 and a back belt 86 (hereinafter may be referred to as "front and back belts"), the front and back belts 84, 86 forming a discrete ring-like elastic belt 40 (hereinafter may be referred to as "waist belt") extending transversely defining the waist opening. For the belt-type pant, the discrete ring-like elastic belt 40 may also be referred to as the elastic belt region 40. For the belt-type pant, the front and back belts 84, 86 and the central chassis 38 jointly define the leg openings. The wearable article 20 may be a uni-body type pant wherein the central chassis 38 is continuous with the front and back belt 84, 86, wherein the leg openings are continuously formed. For the uni-body pant, the belt portion existing between the side seams are considered the elastic belt region 40, wherein the region is considered to terminate by an imaginary line running in the transverse direction between the proximal edges of the side seams. The remainder of the article except the elastic belt region 40 is considered the crotch region 30.

Figure 3:
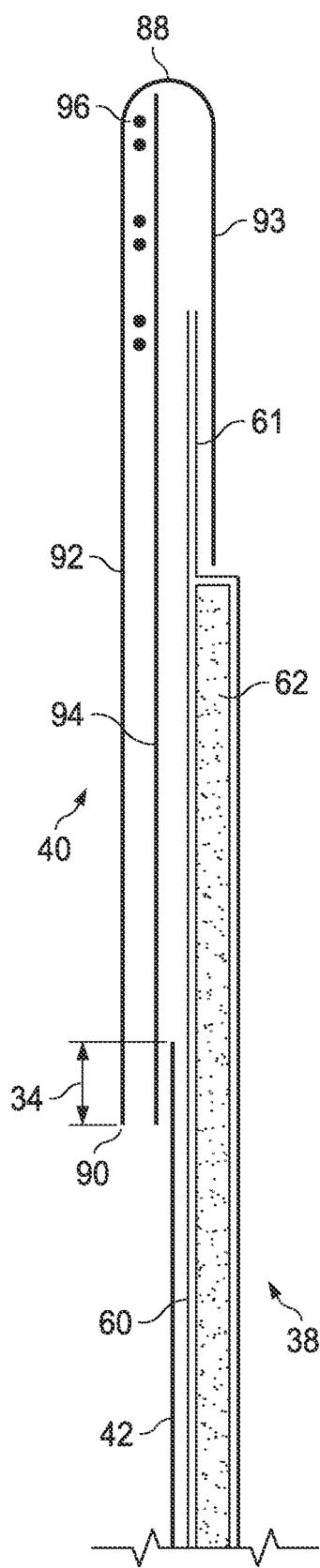
FIG. 3 is a cross section view of FIG. 2 taken along the longitudinal center line.

Referring to FIG. 3, the central chassis 38 comprises a backsheet 60 and an outer cover layer 42 for covering the garment-facing side of the backsheet 60. The backsheet 60 may be a water impermeable film. The outer cover layer 42 may be a nonwoven sheet. The central chassis 38 may contain an absorbent core 62 for absorbing and containing body exudates disposed on the central chassis 38. In the embodiment shown in FIG. 2, the central chassis 38 has a generally rectangular shape, left and right longitudinally extending side edges 48 (hereinafter may be referred to as "side edge") and front and back transversely extending end edges 50 (hereinafter may be referred to as "end edge"). The central chassis 38 also has a front waist panel 52 positioned in the front region 26 of the wearable article 20, a back waist panel 54 positioned in the back region 28, and a crotch panel 56 between the front and back waist panels 52, 54 in the crotch region 30. The center of the front belt 84 is joined to a front waist panel 52 of the central chassis 38, the center of the back belt 86 is joined to a back waist panel 54 of the central chassis 38, the front and back belts 84, 86 each having a left side panel and a right side panel 82 where the central chassis 38 does not overlap.

The elastic belt region of the article of the present invention acts to dynamically create fitment forces and to distribute the forces dynamically generated during wear. The proximal edge 90 is located closer than the distal edge 88 relative to the crotch panel 56 of the central chassis 38. The front and back belts 84, 86 may be joined with each other only at the side edges 89 at the seams 32 to form a wearable article having a waist opening and two leg openings. Each leg opening may be provided with elasticity around the perimeter of the leg opening. For the belt-type pant, the elasticity around the leg opening may be provided by the combination of elasticity from the front belt 84, the back belt 86, and any from the central chassis 38.

The transverse width of the backsheet 60 and the outer cover layer 42 may be the same, or may be varied (not shown). For example, the backsheet 60 may have a shorter transverse width compared to that of the outer cover layer 42. By such configuration, the longitudinal side edges 48 of the crotch panel 56, which make part of the leg openings, may have better breathability. Further, such configuration may provide cost saving.

The front belt 84 and back belt 86 are configured to impart elasticity to the belt 40. The front belt 84 and the back belt 86 may each be formed by a laminate comprising a plurality of elastic bodies 96 running in the transverse direction, an inner sheet 94, an outer sheet 92, and an outer sheet fold over 93 wherein the outer sheet fold over 93 is an extension of the outer sheet material formed by folding the outer sheet material at the distal edge 88 of the front and back belts; wherein the belt elastic bodies 96 are sandwiched between two of these sheets. The front belt 84 and the back belt 86 may each be made only by elastic bodies 96, the inner sheet 94, the outer sheet 92, and the outer sheet fold over 93. The belt elastic bodies 96 may extend in the transverse direction to provide a ring like elastic belt 40 when the front belt 84 and the back belt 86 are joined. At least some of the elastic bodies 96 extend in the transverse direction substantially parallel to each other. All of the elastic bodies 96 may extend in the transverse direction substantially parallel to each other. Such an article may be economically made. The front and back belt 84, 86 each may have transversely continuous proximal and distal edges, the proximal edge 90 being located closer than the distal edge 88 relative to the longitudinal center of the article. The elastic bodies 96 may be disposed in the same or different denier, interval, and force between the front and back, as well as in different longitudinal positions of the belt.

The front and/or back belt 84, 86 may be treated such that certain of the area overlapping the front and/or back waist panel 52, 54 of the central chassis 38 are removed of elasticity. Removal of elasticity from a certain area of the front and/or back waist panel 52, 54 may be advantageous when the central chassis 38 comprises an absorbent core 62, in that elasticity in the front and/or back area overlapping the absorbent core 62 may cause bunching of the absorbent layer or any of the layers in the absorbent core 62 and interfere with close fit of the central chassis 38 to the wearer. In one embodiment, at least a portion of, or at least 10% of, or at least 20% of, or at least 30% of, the elasticity of; at least one of, or at least half of, or at least two thirds of, the elastic bodies are removed in the region overlapping with the front and back waist panels 52, 54 of the central chassis 38. Referring to FIG. 2, the entire area where the elastic bodies 96 overlap with the absorbent core 62 may be removed of its elasticity as in the front belt 84. Alternatively, as seen in the back belt 86, the elastic bodies 96 overlapping the absorbent material non-existing region 61 and toward the distal edges of the absorbent core 62 may be disposed in active elasticity for good fit of the central chassis 38. This may be advantageous in preventing leakage.

Referring to FIG. 2, the transverse width LW of the back belt 86 in the uncontracted condition may be the same as the transverse width of the front belt 84 of the same condition. Such an article may be economically made.

The longitudinal length LB of the back belt 86 between the back distal edge 88 and the back proximal edge 90 along its entire width LW of the back belt 86 may be approximately the same as the longitudinal length LF of the front belt 84 between the front distal edge 88 and the front proximal edge 90. In such configuration, the seams 32 close the front and back belt 84, 86 side edges 89 of the same length for forming the article. Such an article may be economically made.

The back belt 86 may have a greater longitudinal length LB between the back distal edge 88 and the back proximal edge 90 along its entire width LW of the back belt 86 in the transverse direction than the longitudinal length LF of the front belt 84 between the front distal edge 88 and the front proximal edge 90 (FIGS. 1 and 2). In such configuration, when the wearable article is assembled to form the waist opening and the leg openings, the wearable article 20 is folded along the transverse centerline T1 such that the front distal edge 88 is aligned with the back distal edge 88. The front side edge 89 is also aligned with a portion of the back side edge 89. Then the front belt 84 and the back belt 86 are joined at the front and back side edges 89 at the seams 32. The front and back proximal edges 90, however, may not be aligned to one another. The back proximal edge 90 may be disposed longitudinally closer than the front proximal edge 90 relative to the transverse center line T1 such that the proximal portion of the back side panel 82 extends toward the crotch panel 56 of the central chassis 38 beyond the front proximal edge 90. The side edge of the proximal portion of the back side panel 82 may not be joined to anywhere and free from attachment. Thus, the proximal portion of the back side panel 82 provides a buttock cover 95 as in FIG. 1.

Whether or not the longitudinal length LB of the back belt 86 and the longitudinal length LF of the front belt 84 are the same, the entirety of the longitudinal length LF of the belt side edge 89 of the front belt 84 is seamed with the belt side edge 89 of the back belt 86 to define a seam length LS. When the front belt 84 has straight distal edges 88 and proximal edges 90 that are substantially parallel with each other, then the longitudinal length LF of the front belt 84 is equal to the seam length LS.

The elastic belt region 40 may be closely associated with the function and quality of the article. Thus, materials for forming the elastic belt region, as well as the elastic profile of the elastic belt region, are carefully selected by the manufacturer for providing the desirables for the article. An undergarment kind of appearance and pleasant tactile sense such as flexibility and cushiony touch may be associated with high quality. Ease of stretch and application, while also maintaining certain force during wear to prevent the article from sagging after loading, may be associated with high function. The balance of the aforementioned quality and function attributes provide the favorable entire usage experience of the article by the user. The user may be the wearer or the caregiver.

The elastic belt region 40 of the article of the present invention may have a Compression Work index of at least about 70 gfcm, or at least about 75 gfcm, and a Stretch Circumference Force of less than about 6.5N, according to the measurements herein. The Compression Work index is for measuring the compression work provided to the elastic belt region 40 by a given force, or the amount of total deformation provided to the elastic belt region 40 by a given force. Measurement for the Compression Work index is conducted at a site wherein a 200 mm² circular plunger 304 touches imaginary lines of: a transversely extending line 30 mm proximal from the front waist edge 88 and a longitudinally extending line 10 mm inward of the side seam 32. This is believed to be the area where the quality of the elastic belt region may be suitably measured. Without being bound by theory, it is believed that the higher the Compression Work index, the more work the elastic belt region can receive and absorb, thus softer the perception of the elastic belt region by the user. The Stretch Circumference Force is for measuring the loading force at a certain stretch level which is believed to simulate initial stretch experience felt by the user when inserting hands and stretch opening the article. Without being bound by theory, it is believed that the lower the Stretch Circumference Force, the elastic belt region may be stretched with less force, thus softer the perception of the elastic belt region by the user.

The elastic belt region 40 of the article of the present invention may have a Drapability index of less than about 25%, or less than about 12% according to the measurements herein. The Drapability index is for measuring the drape property, or flexibility of the belt elastic region 40 of the article. Measurement for the Drapability index is conducted at a site wherein a 10 mm×50 mm drape plunger touches imaginary lines of: a transversely extending line 30 mm proximal from the front waist edge 88 and a longitudinally extending line 10 mm inward of the side seam 32. Similarly to the Compression Work index, this is believed to be the area where the quality of the elastic belt region may be suitably measured. Without being bound by theory, it is believed that the lower the Drapability index, the more flexible the elastic belt region is, and the soft undergarment like tactile sense is provided to the elastic belt region. The Compression Work index and the Drapability index are intended to measure different types of softness perception of the user.

The elastic belt region of the article of the present invention may have a Compression Work index of at least about 70 gfcm, a Drapability index of less than about 25%, and a Stretch Circumference Force of less than about 7.0N according to the measurements herein.

As mentioned above, the article of the present invention may have a suitable Stretch Circumference Force (N). What is meant by Stretch Circumference Force is the loading force at a certain stretch level which is believed to simulate initial stretch experience felt by the user when inserting hands and stretch opening the article. The level of stretch which is believed to be felt by the user when stretch opening the article is represented by the "470 mm Stretch Circumference". The dimension of 470 mm is selected based on a study by the Applicant whereby the average standing hip circumference (mm) at the height matching the pubic bone of children having a body weight of 6-20 kg was 473 mm based on data from over 1000 subjects. Namely, according to common habits for wearing a pant article, the user would stretch open the elastic belt region of the pant article to a circumference more or less matching that of the hip circumference of the body of the wearer. A body weight of 6-20 kg matches the recommended body weight of wearers for pant articles of Sizes 3-6 (Sizes M to XXL). The article of the present invention has a Stretch Circumference Force of no greater than about 7N, or no greater than about 6.5N, or no greater than about 6N. By having such Stretch Circumference Force, the elastic belt can be easily opened and applied.

The article of the present invention may have a suitable Fit Circumference Force (N). What is meant by Fit Circumference Force is the unloading force at a certain stretch level which is believed to simulate the force felt by the wearer while wearing the article. The level of stretch which is believed to be felt by the wearer while wearing the article is also represented by the 470 mm Stretch Circumference. The article of the present invention has a Fit Circumference Force of no less than about 2N. By having such Fit Circumference Force, the elastic belt provides good fit to prevent sagging and leakage. Without being bound by theory, it is believed that by having a relatively low Stretch Circumference Force of no greater than about 6.5N in combination with a minimum Fit Circumference Force of no less than about 2N, an elastic belt region having ease of application and a secure yet soft fit may be provided.

The article of the present invention may have at least a certain Full Circumference (mm). The Full Circumference is meant to measure the maximum circumference to which the article may be stretch opened. The article of the present invention may have a Full Circumference of from about 610 mm to about 670 mm for Size 3 (or M size, for wearers of body weight 6-11 kgs), or from about 660 mm to about 720 mm for Size 4 (or L size, for wearers of body weight 9-14 kgs), or from about 710 mm to about 760 mm for Size 5 (or XL size, for wearers of body weight 12-17 kgs).

The Full Circumference (mm), 470 mm Stretch Circumference (mm), Fit Circumference Force (N), and Stretch Circumference Force (N), are obtained according to the "Whole Article Force Measurement" below.

The tensile stress (N/m) of the front and back elastic belts 84, 86, respectively, may be profiled in order to provide the benefits of the present invention. When the front and back belts 84, 86 form a ring like elastic belt wherein all of the elastic bodies sandwiched between the inner sheet 94 and the outer sheet 92 run in the transverse direction substantially parallel to each other, the tensile stress may be measured, for example, by the Zone Tensile Stress Measurement described herein below. When the elasticity of the front and back elastic belts 84, 86 are provided by a plurality of elastic bodies 96 running in the transverse direction, the tensile stress may be adjusted by one or more of the following methods; 1) elongation rate of the elastic body 96; 2) density (dtex) of the elastic body 96; 3) longitudinal interval of multiple elastic bodies 96; and 4) effective length of elasticity of the elastic body 96 in the transverse direction. By elongation, "0% elongation" is meant the original length of the elastic body. When a portion of an elastic body is removed of its elasticity, the remainder of the intact elastic body capable of imparting elasticity is defined as the "effective length of elasticity of an elastic body". The elastic bodies 96 disposed on the front and/or back belt 84, 86 may be treated such that certain of the area overlapping the front and/or back waist panels 52, 54 of the central chassis 38 are removed of elasticity. Removal of elasticity from at least a portion of the area overlapping the front and/or back waist panel 52, 54 of at least one elastic body may be advantageous when the central chassis 38 comprises an absorbent core 62, in that elasticity in the front and/or back area may cause bunching of the absorbent core 62 and interfere with close fit of the central chassis 38 to the wearer. In one embodiment, at least a portion of, or at least 10% of, or at least 20% of, or at least 30% of, the elasticity of; at least one of, or at least half of, or at least two thirds of, or all of, the elastic bodies are removed in the region overlapping with the front and back waist panels 52, 54 or the absorbent core 62 of the central chassis 38.

Figure 4:
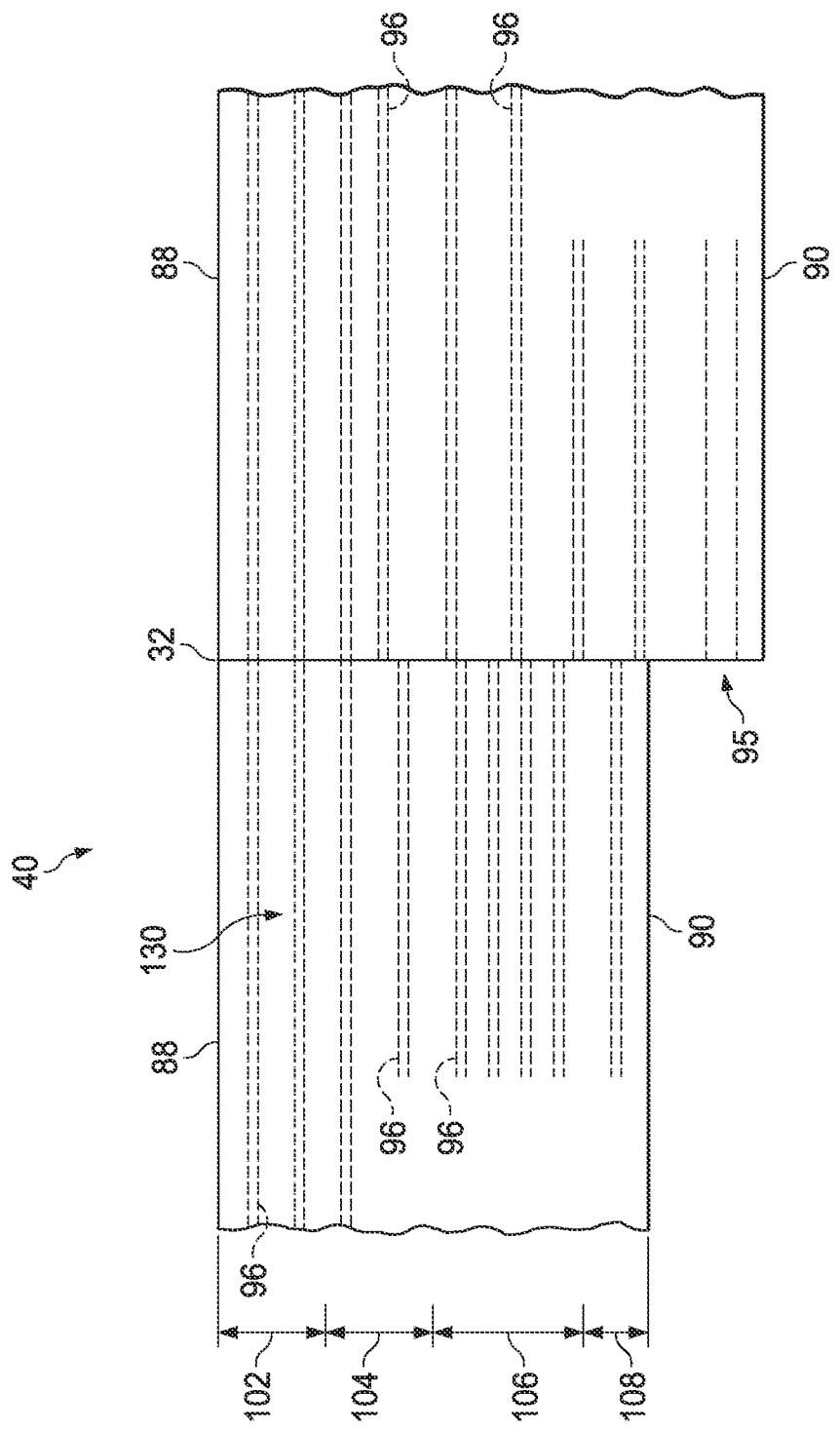
FIG. 4 is a schematic side plan view of one embodiment of a wearable article of the present invention in a flat uncontracted condition showing the garment facing surface.

Referring to FIG. 4, the front and back belts 84, 86 are each divided into 4 zones extending in the transverse direction and defined of its position from the distal edge 88 to the proximal edge 90 relative to the percentage of the seam length LS. The entirety of the length of the belt side edge 89 of the front belt 84 is seamed with a certain length of the belt side edge 89 of the back belt 86 to define a seam length LS. When seam length LS is considered 0% at the distal edge 88 and 100% at the proximal edge 90 of the front belt 84, the zones are defined as such: 0-25% is the waist zone 102, 25-50% is the distal tummy zone 104, 50-85% is the proximal tummy zone 106, and 85-100% is the leg zone 108. When there is an elastic body disposed at 25% from the distal edge 88, such elastic body is considered to be included in the waist zone 102. When there is an elastic body disposed at 50% from the distal edge 88, or 85% from the distal edge 88, such elastic body is considered to be included in the proximal tummy zone 106. For embodiments where the back belt 86 has a greater longitudinal length LB than the longitudinal length LF of the front belt 84, the remaining length of "LB minus LS" of the back belt 86 is not counted in the 4 zones described above.

The article of the present invention may have a plurality of elastic bodies disposed on each of the zones for providing tensile stress to the elastic belt region. The elastic bodies disposed on the front proximal tummy zone 106 may have a density of no less than about 540 dtex. The elastic bodies on the front proximal tummy zone 106 may be disposed at an elongation of from about 150% to about 250%. In one embodiment, from 6 to 18 elastic bodies may be disposed on the front proximal tummy zone 106. Some elastics may be disposed to impart higher tensile stress in certain regions. Such one or more elastics of higher tensile stress may be disposed in an array of 2-4 elastic strands having an interval within the array of between 2-4 mm. The array may be disposed on the front proximal tummy zone 106. The array may be disposed on the back distal tummy zone 104.

In the article of the present invention, the tensile stress of the front proximal tummy zone 106 may be higher than the tensile stress of any other zone, in the front or the back. The tensile stress of the front proximal tummy zone 106 may be no less than about 200% of the tensile stress of the front distal tummy zone 104. The tensile stress of the front distal tummy zone 104 may be lower than, or no more than about 70% of, the tensile stress of the back distal tummy zone 104. The tensile stress of the front proximal tummy zone 106 may be no less than about 150% of the tensile stress of the back proximal tummy zone 106. The tensile stress of the front leg zone 108 may be from about 80% to about 200% of the tensile stress of the back leg zone 108. In one embodiment, the tensile stress of the front waist zone 102 may be from about 80% to about 120% of the tensile stress of the back waist zone 102.

Figure 5:
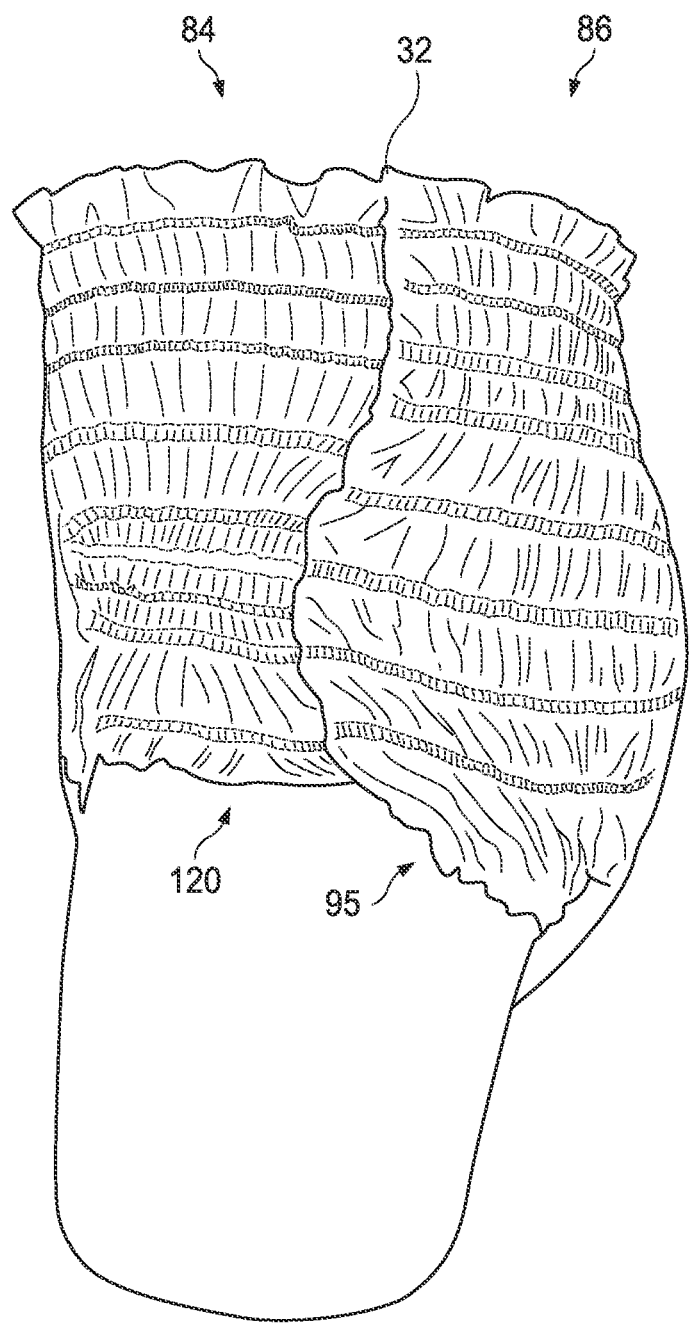
FIG. 5 is a side view of one embodiment of a wearable article of the present invention worn on a mannequin.

Referring to FIG. 5, without being bound by theory, such profiling of the tensile stress per zone is believed to provide the article of the present invention with a shaped elastic belt 40 that conforms well to a human body, particularly to a lower torso of a child of less than 36 months of age, and therefore provide good fit and comfort to the wearer, without compromise of sagging prevention or leakage prevention. Namely, the front proximal tummy zone 106 is subject to high tensile stress such that the article may be anchored against the wearer's trochanter, while leaving more area for the back proximal tummy zone 106 to accommodate the wearer's buttock. As long as the article is anchored securely at the trochanter, the leg zone 108 adjacent the leg opening may be provided with significantly less tensile stress compared to the proximal tummy zone 106. Thus, the soft fit at the front leg opening region 120 facilitates leg movement. Further, by providing a higher tensile stress to the back distal tummy zone 104 compared to the front distal tummy zone 104, the wearer's front waist area is accommodated.

As a result of the profiling as described above, the article of the present invention may take an S-curve side seam 32 observed by the side when worn by the wearer. In that the front belt 84 is pulled toward the front side due to the highest tensile stress in the article of the front proximal tummy zone 106, the remainder of the side seam 32 may be curved accordingly. When the waist belt 40 of the present invention is measured against the Belt Seam Shape Measurement method described below, the d value may be no less than about +10 mm, or no less than about +15 mm, or no less than about +20 mm Such d value is indicative of the article conforming to the relatively greater front waist area and greater buttock area of the wearer, while providing good anchoring at the front proximal tummy zone 106. The curved side seam 32 and positive d value is observed no matter how the stretch board 180 is inserted in the sample, so long as a certain amount of time is allowed for the sample to reach equilibrium. Such behavior of the waist belt 40 of the present invention is in contrast with many wearable articles available in the market, wherein the side seam takes a relatively straight line, or a line slightly slanted toward the back. For such articles with side seams taking a relatively straight line, the d value according to the Belt Seam Shape Measurement herein may be negative.

The elastic profiling described herein may be utilized for economically making an article having a longitudinal length of no less than 420 mm, or no less than 450 mm, or no less than 500 mm in the longitudinal axis by using a total of no more than 60, or no more than 46 elastic bodies for the elastic belt 40 per article. The article of the present invention may have an entire longitudinal length of the article of from 350 mm to 600 mm, an effective transverse belt width (LW) of from 315 mm to 500 mm, a back belt longitudinal length (LB) of from 100 mm to 180 mm, a front belt longitudinal length (LF) of from 80 mm to 160 mm, a central chassis longitudinal length of from 310 mm to 560 mm, and a central chassis transverse width of from 150 mm to 210 mm. The article of the present invention may have a distance between the distal edge of the front belt to the longitudinal edge of the central chassis of from 0 mm to 70 mm, and a distance between the distal edge of the back belt to the longitudinal edge of the central chassis of from 0 mm to 90 mm, and such distances on the front and back belt may be the same or different. The longitudinal length of the central chassis may be from 70% to 100% of the entire longitudinal length of the article. When the central chassis comprises an absorbent core 62, the core may have a longitudinal length of from 270 mm to 500 mm, a maximum transverse width of the core of from 90 mm to 125 mm, and a distance between the longitudinal edge of the core to the longitudinal edge of the central chassis of from 10 mm to 40 mm. The longitudinal length of the core may be from 60% to 95% of the entire longitudinal length of the article, or from 66% to 97% of the central chassis.

In the present invention, the elongation of the elastic bodies disposed on the front and back of the same zone may be substantially matched. When a certain length of the elastic body is removed of its elasticity, the effective length of elasticity of such elastic body is considered. By matching the elongation rate of the elastic bodies disposed on the front and back of the same zone, and having the front and back belt 84, 86 have the same width LW, the article 20 may be manufactured such that in the unstretched, contracted condition, the article 20 can be flattened. The aforementioned shaping effect of the article 20 conforming to the wearer's body shape is exerted only when the article 20 is in the stretched, wearable condition. Such flattening capability is found for many commercially available pant-type wearable articles, and provides many benefits for providing the article economically. The capability of being flattened accommodates assembling, transferring, and packaging of the article 20.

The obtained wearable article of the present invention may provide high quality perception, overall softness, ease of application, fit, comfort during wear, easy movement during wear, prevention of sagging, and prevention of leakage.

The outer sheet 92 for forming the elastic belt region 40 may have a certain material thickness to provide the lofty undergarment-like appearance and feel, for example, at least about 0.25 mm, or at least about 0.3 mm. The material thickness herein is related to materials obtained from a finished product according to the "Preparation for Thickness and Basis Weight" below and measured by "Base caliper method—ASTM D 654 Standard Test Method for Thickness of Paper and Paper Board" with modification of the loading to 500 Pa. Suitable for the outer sheet 92 of the present invention include: hi-loft nonwoven, air-through carded nonwoven, and spunbond nonwoven made of crimping fiber made through core eccentric bicomponent filament or side by side bicomponent filament, preferably air-through carded nonwoven. Non-limiting examples of materials suitable for the outer sheet 92 include: 20-50 gsm air-through carded nonwoven made of less than 15 µm diameter PE/PET bi-component staple fiber, such as those with a tradename of FJ206 available from Dayuan, Beijing China.

The inner and outer sheets 92, 94 may be the same or different material, and selected to provide characteristics such as breathability, softness, cushiony feel, loftiness, and combinations thereof, depending on the desirables of the resulting article. The inner and outer sheets 92, 94 may have the same or different basis weight, stiffness, texture or any combination thereof. The outer sheet 92 may have higher basis weight than the inner sheet 94 for providing the favorable tactile acceptance as discussed above, while controlling cost.

Suitable for the inner sheet 94 of the present invention include: 10-40 gsm soft nonwoven, spunbond nonwoven with filament additive slip agent, spun high-loft nonwoven or air-through carded nonwoven, preferably spun high-loft nonwoven.

The material for the outer cover layer 42 may be selected to provide characteristics such as breathability, softness, cushiony feel, loftiness, and combinations thereof, depending on the desirables of the resulting article. The outer cover layer 42 may be made of the same material as the outer sheet 92 to provide integral aesthetic and tactile senses for the article. By "the same material", what is meant is that the nonwoven has the same type of filament in shape, composition, diameter difference of no more than 2 µm, and basis weight difference of no more than 2 gsm. Such comparison of the materials is made by analyzing the materials by SEM and FTIR measurements as detailed below. The basis weight herein is related to materials obtained from a finished product according to the "Preparation for Thickness and Basis Weight" below and measured by "Basis weight— ASTM D 756 Practice for Determination of Weight and Shape Changes of Plastics Under Accelerated Service Conditions".

Referring to FIG. 3, for the belt-type pant the front and back belts 84, 86 are discontinuous with one another in the crotch region 30, and the outer cover layer 42 is the garment-facing surface in the crotch region 30. The outer cover layer 42 may extend only partly in the longitudinal direction of the front waist panel 52 and the back waist panel 54 to leave the distal parts of the front waist panel 52 and the back waist panel 54 free of the outer cover layer 42. Namely, the longitudinal length of the outer cover layer 42 may be longer than the longitudinal length of the crotch panel 56 and shorter than the longitudinal length of the backsheet 60. By such configuration, the distal parts of the front waist panel 52 and the back waist panel 54 are devoid of the outer cover layer 42, providing better breathability to the overall article. Further, this may provide cost saving of the outer cover layer 42 material. Accordingly, looking at the layers of elements between the garment facing surface and the backsheet of the center chassis 38 of FIG. 3, there exists a transitional region 34 disposed on the waist panel 52 where the outer cover layer 42 is present. The longitudinal length of the transitional region 34 may be made as short as possible, for example, less than about 20 mm, or less than about 15 mm, or less than about 10 mm. Further, adhesive may be applied on the entire area of the transitional region 34, or the entire area leaving no more than up to 5 mm, in the longitudinal direction, from the distal edge of the transitional region 34. For providing attractive artwork for a wearable article in an economical manner, printing may be provided on the garment facing side of the backsheet 60. By providing the transitional region 34 as short as possible, applying adhesive to the transitional region 34 to enhance transparency, or simply avoiding displaying artwork in the transitional region 34, compromised appearance of the artwork over different layers of material between the artwork and the observer may be avoided. Referring to FIG. 2, artwork on the backsheet 60 may be printed in regions 40F or 40B.

Alternatively, when artwork provided on the backsheet 60 extends across the elastic belt region 40 and the crotch region 30, the area of the artwork in the belt region 40 may be provided in reduced brightness and increased contrast compared to the area in the crotch region 30; such that the intensity of the artwork appear to be substantially similar when observed as an article from the garment facing side. By providing the artwork in reduced brightness and increased contrast, the artwork is less influenced by opaqueness provided by the overlaying layers of material.

Alternatively and/or additionally, the artwork in the elastic belt region 40 may be printed on the garment facing surface of the inner sheet 94 or the body facing surface of the outer sheet 92, and the artwork in the crotch region 30 may be printed on the backsheet 60. By printing the artwork in these specific layers, the number of layers between the garment facing surface and the printing may be made equal, thus the appearance difference may be alleviated. The opacity difference between the outer sheet 92 and the outer cover layer 42 may be minimized by selecting the layers to match the opacity, or by disposing the same material. The artwork for the elastic belt region 40 may be printed directly on the inner sheet 94 or the outer sheet 92 by ink, or by disposing a colored web of a predetermined shape.

As mentioned above, the front belt may have a longitudinal length of LF; and the back belt may have a longitudinal length of LB, and the outer sheet fold over 93 is formed by folding the outer sheet material at the distal edge 88 of the front and back belts. The front outer sheet fold over 93 may have a longitudinal length of at least about 0.3 LF, or from about 0.3 LF to about 0.7 LF, or from about 0.5 LF to about 0.7 LF. The back outer sheet fold over 93 may have a longitudinal length to match the length of the front outer sheet fold over 93. Namely, the back outer sheet fold over may have about the same length as the front outer sheet fold over.

The articles of the present invention provide overall softness, being easy to apply, comfortable for the wearer to wear, allowing the wearer to move at ease, and the perception of undergarment like, and overall high quality.

1. Preparation for Thickness and Basis Weight

The following sampling procedures are taken for measuring thickness and basis weight of a material used in a finished product.

To obtain a sample from a finished article, when available, an area free of deformation or wrinking is selected. For the belt elastic region 40, when available, area where the elasticity is deactivated is selected. The outer sheet 92, inner sheet 94, or outer cover layer 42 is separated from the other components such as belt laminated nonwoven layers, or backsheet film by techniques such as applying "Quik-Freeze®" type cold spray, or other suitable methods that do not permanently alter the properties of the nonwoven composition. The technical face-side is the surface intended to be used as the garment-facing surface for the outer sheet 92 or outer cover layer 42, and the body-facing surface for the inner sheet 94. Care should be taken to prevent stretching of the nonwoven composition during the separation process. A 100 mm by 100 mm square shape is cut out using a cutter and a 100 cm² die for obtaining the sample.

For measuring the basis weight, any remaining adhesive is removed from the sample by the following steps using Tetrahydrofuran (THF) as solvent.

1. In a hood, transfer 1 liter of THF into the 3-4 liter beaker
2. Submerge sample in the 1 liter of THF
3. Place beaker on shaking table and stir gently for 15 minutes and keep solution with sample sit for 5 additional minutes
4. Take sample out of THF solution, and carefully squeeze THF solution out of sample.
5. Let sample air dry in hood for a minimum of 15 minutes Samples are obtained from ten (10) finished products from the same package and cut out from the same area of each article, for each set of measurement. Samples are pre-conditioned in a room maintained at about 23±2° C. and about 50±5% relative humidity, for at least 2 hours prior to testing.

2. Compression Work Index

The method is to measure compression property, or Compression Work Index, for the elastic belt region of the sample article. Force is measured using an Electronic Tensile Tester with a computer interface such as the MTS Criterion C42 running TestWorks 4 Software (available from MTS SYSTEMS (CHINA) CO., LTD) or equivalent instrument. A load cell is selected so that force results for the samples tested will be between 10 and 90% of capacity of the load cell used. The instrument is calibrated according to the manufacturer's instructions. All testing is performed in a room maintained at 23±2° C. and 50±5% relative humidity. Samples are pre-conditioned in a room maintained at 23±2° C. and 50±5% relative humidity, for at least 2 hours prior to testing. Samples are used as immediately taken out from a package with no treatment.

Figure 6A:
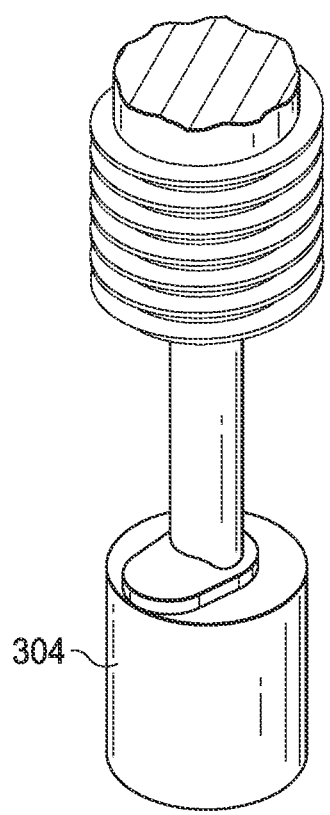
FIGS. 6A-6D are schematic views of examples of equipment according to the "Article Compression Test" and "Article Drapability Test".
Figure 6B:
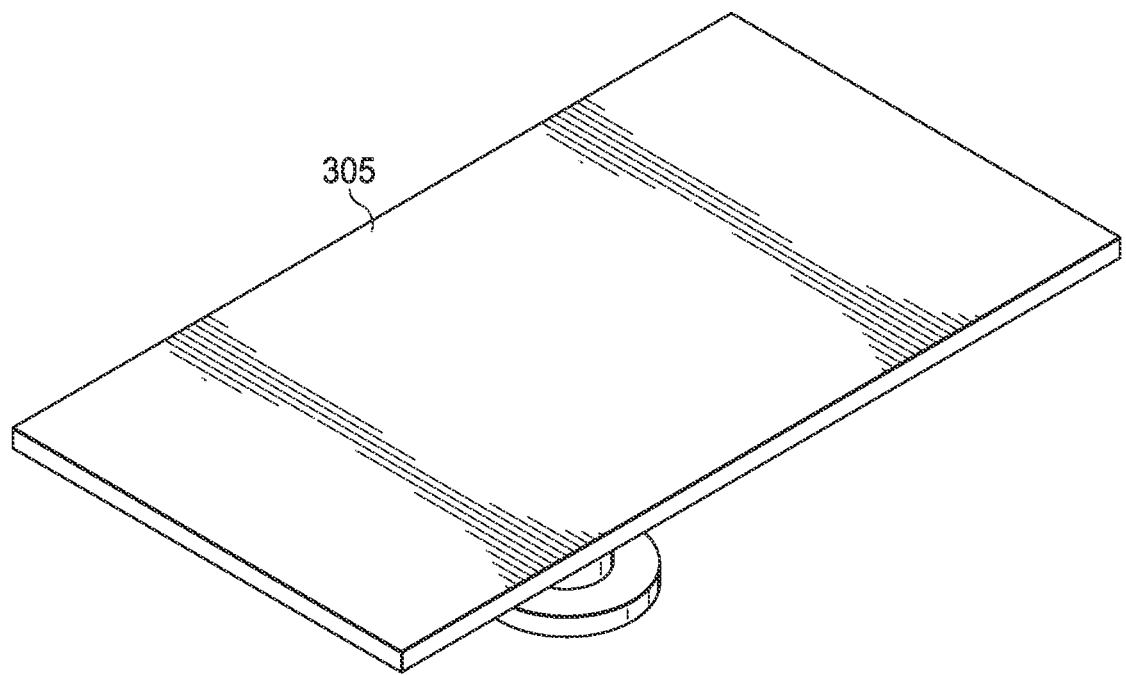

Referring to FIGS. 6A and 6B, the tensile tester is fitted with a plunger (custom made 200 mm² circular plunger 304) for the upper fixture, and a stage (150 mm×310 mm stage 305) for the lower fixture. The instrument is set up to go through the following steps:

| | |
|---|---|
| Crosshead Speed | 0.2 mm/sec |
| Pre-load | 1 gf |
| Final Load Point | 400 gf |
| Hold Time | 0 |
| Number of Cycles | 1 |
| Data Acquisition Rate | 50 Hz |

The crosshead is drawn down to a position such that the circular plunger 304 is close to, but not touching, the stage 305. This is to minimize the time the circular plunger 304 moves to reach the stage 305 at the beginning of the test procedure. Measure the rough thickness of the sample article using ruler. The rough thickness of the sample plus 1 mm is the "platen separation" value. Set the movement of circular plunger 304 to initially reach to the stage 305, then go up until the predetermined "platen separation" value is provided between the circular plunger 304 and the stage 305. Insert sample between the circular plunger 304 and stage 305 such that the circumference of the circular plunger 304 touches imaginary lines of: a transversely extending line 30 mm proximal from the front waist edge and a longitudinally extending line 10 mm inward of the side seam. Set the crosshead travel to compress the sample article until the load exceeds 400 gf, then return to the "platen separation" position.

Five samples are analyzed and the Compression Work index are calculated and reported to the nearest 0.1 gfcm.

Compression Work Index: During the compression process, total work done on the sample. Integral of the compression curve.

$$CW = \int_{Da}^{Dc} P\,dD$$

wherein Da is the initial thickness when the load cell detects 1 gf, Dc is minimum thickness at maximum load of 400 gf, P is the measured load and D is the measured thickness during the compression test.

3. Drapability Index

The method is to measure drape property, or Drapability index, for the belt elastic region of the article. Force is measured using an Electronic Tensile Tester with a computer interface such as the MTS Criterion C42 running TestWorks 4 Software (available from MTS SYSTEMS (CHINA) CO., LTD) or equivalent instrument. A load cell is selected so that force results for the samples tested will be between 10 and 90% of capacity of the load cell used. The instrument is calibrated according to the manufacturer's instructions. All testing is performed in a room maintained at 23±2° C. and 50±5% relative humidity. Samples are pre-conditioned in a room maintained at about 23±2° C. and about 50±5% relative humidity, for at least 2 hours prior to testing. Samples are used as immediately taken out from a package with no treatment.

Figure 6C:
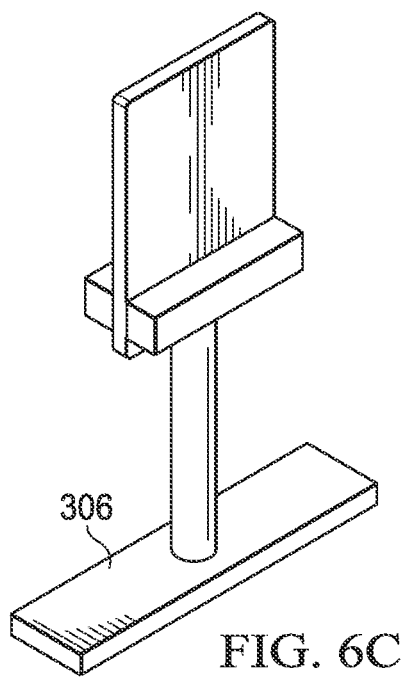
Figure 6D:
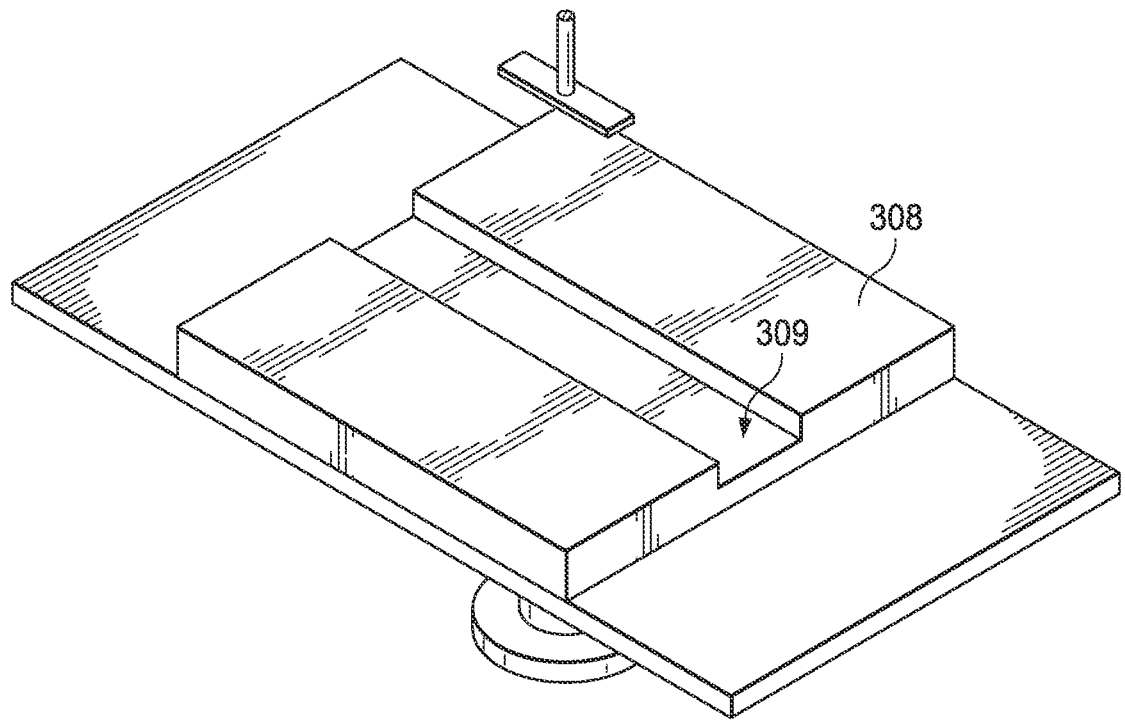

The tensile tester is fitted with plunger and stage as shown in FIGS. 6B and 6C. The upper jaw is replaced with a 25.4×25.4 mm square jaw area and connected to a drape plunger 306 having an area of 10 mm×50 mm, custom made. The lower jaw is replaced with a 150 mm×310 mm stage 305. Referring to FIG. 6D, a drape plate 308 having an area of 140 mm×140 mm is placed on the stage, the drape plate 308 having a slot 309 in the middle of drape plate having a dimension of: 140 mm length, 30 mm width, and 8 mm depth. The drape plate 308 is aligned position with the drape plunger 306 such that the drape plunger 306 may fit the slot 309 when moved down. The instrument is set up to go through the following steps.

| | |
|---|---|
| Crosshead Speed | 0.3 mm/sec |
| Pre-load | 1 gf |
| Final Load Point | 1000 gf |
| Hold Time | 0 |
| Number of Cycles | 1 |
| Data Acquisition Rate | 50 Hz |

Figure 7:
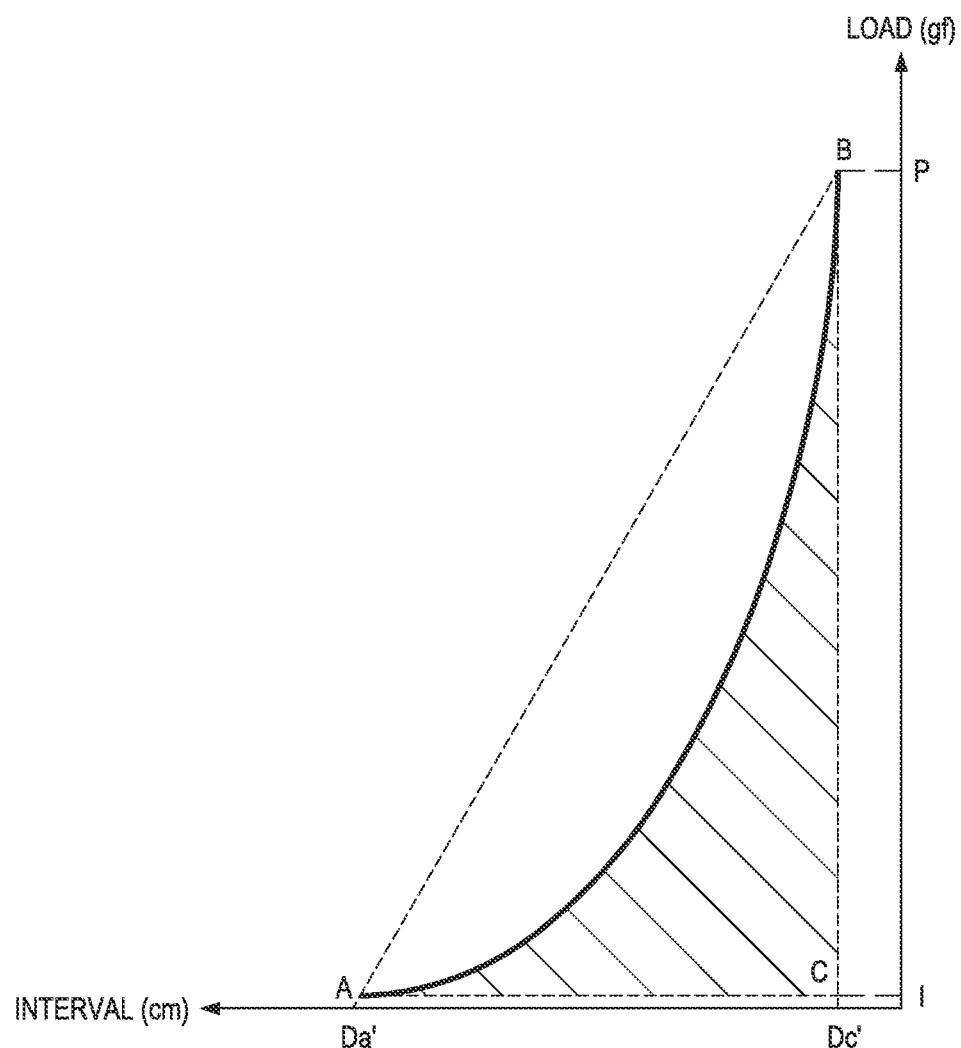
FIG. 7 is a conceptual chart of the Drapability index parameter of the present invention.
Figure 8:
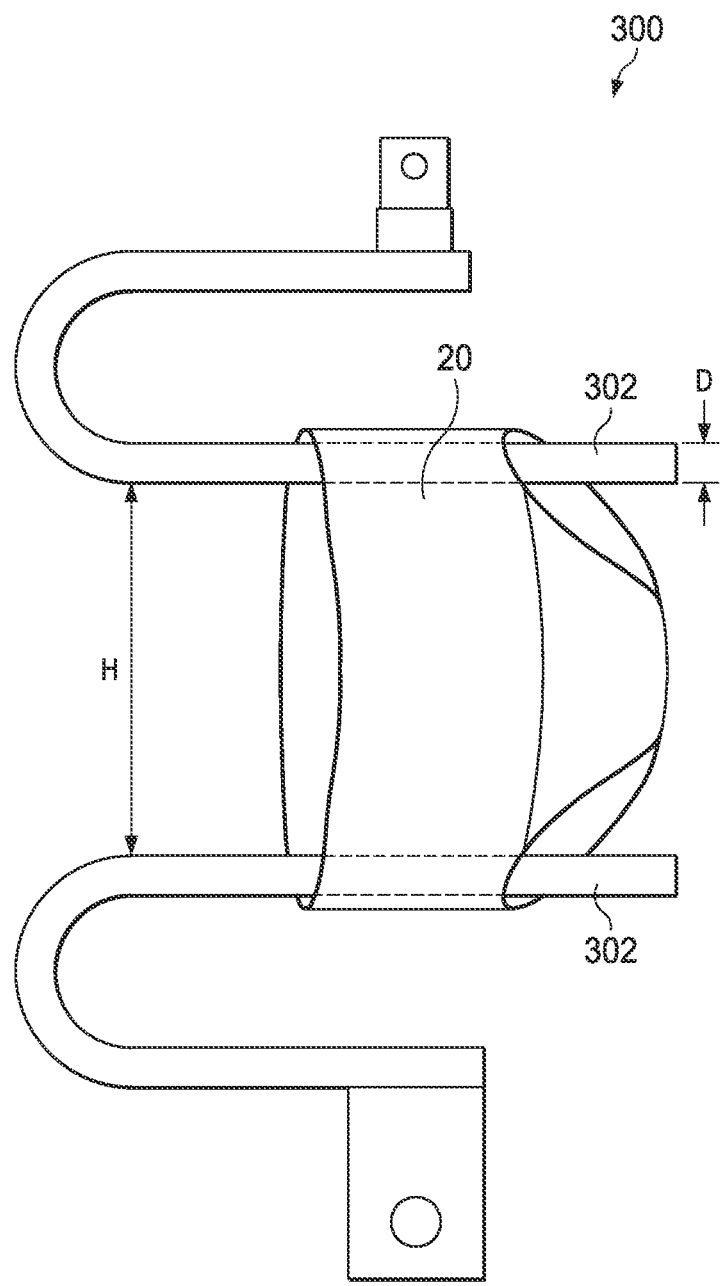
FIG. 8 is a schematic view of an example of a hanger-type sample holding fixture according to the "Whole Article Force Measurement".

The crosshead is drawn down to a position such that the drape plunger 306 is close to, but not touching, the stage 305. Measure the rough thickness of the sample article using ruler. The rough thickness of the sample plus 8 mm is the "platen separation" value. Set the movement of drape plunger 306 to initially reach the drape plate 308, then go up until the predetermined "platen separation" value is provided between the drape plunger 306 and the drape plate 308. Insert sample between the drape plunger 306 and the drape plate 308 such that the circumference of the drape plunger 306 touches imaginary lines of: a transversely extending line 30 mm proximal from the front waist edge and a longitudinally extending line 10 mm inward of the side seam. Set the crosshead travel to compress the sample article until the load exceeds 1000 gf, then return to the "platen separation" position. Five samples are analyzed and Linearity of Compression (LC) is calculated and reported to the nearest 0.1%.

$$LC = \frac{100 \times CW}{\text{Area of triangle } ABC} \%$$

herein CW (gfcm) is the total work done on the specimen during the measurement process, integral of the compression curve of FIG. 7, wherein Da' is the interval between drape plunger and drape plate when the load cell detect 1 gf, Dc' is the interval between drape plunger and drape plate at maximum load-1000 gf, P is the measured load and D is the measured interval between drape plunger and drape plate during the drape test. A point starts when load cell detects 1 gf. The load cell goes down and makes the curve from A to B when load cell detects 1000 gf.

4. Whole Article Force Measurement

Force is measured using an Electronic Tensile Tester with a computer interface such as the MTS Criterion C42 running TestWorks 4 Software (available from MTS SYSTEMS (CHINA) CO., LTD) or equivalent instrument. A load cell is selected so that force results for the samples tested will be between 10 and 90% of capacity of the load cell used. The instrument is calibrated according to the manufacturer's instructions. All testing is performed in a room maintained at 23±2° C. and 50±5% relative humidity.

The tensile tester is fitted with hanger-type sample holding fixtures 300 as shown in FIG. 7. Each fixture comprises a rigid linear rubber-coated horizontal bar section 302 to prevent sample slippage during testing. The outer bar diameter (including the rubber coating) of the horizontal bar sections is 10.0 mm. The central axes of the horizontal bar sections 302 are configured to remain parallel and in the same vertical plane throughout the test procedure. The gauge circumference is determined by the following equation:

Gauge Circumference=2×(H+D+πD/2)

where H is the vertical gap between the horizontal bar sections 302, and D is the outer diameter of the bar.

The instrument is set up to go through the following steps:

| | |
|---|---|
| Crosshead Speed | 254.0 mm/min |
| Final Load Point | 19.6N |
| Hold Time | 0 |
| Number of Cycles | 1 |
| Data Acquisition Rate | 50 Hz |

A sample article 20 is inserted onto the upper horizontal bar section 302 so that the bar passes through the waist opening and one leg opening of the article. The crosshead is raised until the specimen hangs above the lower bar and does not touch lower bar 302. The load cell is tared and the crosshead is lowered to enable the lower bar 302 to be inserted through the waist opening and other leg opening without stretching the article. The article is adjusted so that the longitudinal centerline L1 of the article is in a horizontal plane halfway between the upper and lower bars 302. The center of the side portion in contact with the bar 302 is situated on the same vertical axis as the instrument load cell. The crosshead is raised slowly while the article is held in place by hand as necessary until the force is between 0.05 and 0.1N, while taking care not to add any unnecessary force. The gauge circumference at this point is the Initial Gauge Circumference. The test is initiated and the crosshead moves up at 254 mm/min until a force of 19.6N is attained, then the crosshead immediately returns to the Initial Gauge Circumference at the same speed. The maximum circumference at 19.6N during the extension segment of the test is recorded.

The maximum circumference at 19.6N is defined as the Full Circumference (mm). The force at a circumference of 470 mm is defined as the 470 mm Stretch Circumference (mm). The Stretch Circumference Force is defined as the force at 470 mm Stretch Circumference during the load (extension) segment of the test. The Fit Circumference Force is defined as the force at 470 mm Stretch Circumference during the unload (contraction) segment of the test.

Five samples are analyzed and their average Initial Gauge Circumference, average Full Circumference, average Stretch Circumference Force and average Fit Circumference Force are calculated and reported to the nearest 1 mm or 0.01 N, respectively.

5. Zone Tensile Stress Measurement

The Zone Tensile Stress Measurement herein is for articles wherein the front belt and the back belt form a ring-like elastic belt, and all of the elastic bodies sandwiched between the inner sheet and the outer sheet run in the transverse direction substantially parallel to each other. The tensile stress (N/m) is calculated by tensile force (N) divided by the longitudinal length (m) of the specimen. Force may be measured using an Electronic Tensile Tester with a computer interface such as the MTS Criterion C42 running TestWorks 4 Software (available from MTS SYSTEMS (CHINA) CO., LTD) or equivalent instrument. A load cell is chosen so that force results for the samples tested will be between 10 and 90% of capacity of the load cell. The instrument is calibrated according to the manufacturer's instructions. All testing is performed in a room maintained at 23±2° C. and 50±5% relative humidity. The instrument is equipped with single line contact grips at least as wide as the test specimen.

To obtain test specimens, the sample article is opened at both side seams in a manner such that the front and back belts are peeled away from each other without removing the side seam area, and the front and rear elastic belts are removed from the central chassis 38 by separating the bonding between the waist belt and central chassis. Cold spray may be used, paying attention not to make wrinkles in the belt sections. Care is taken not to spray on any belt elastic body 96. The obtained elastic belts 40 are severed into zones 102, 104, 106, 108 as defined above with care not to cut any elastic body 96. Samples are pre-conditioned at 23±2° C. and 50±5% relative humidity for two hours prior to testing. Measure the longitudinal length of each specimen by a generic metal ruler to the nearest 1 mm By longitudinal length, what is meant is the dimension 102, 104, 106, or 108 in FIG. 4.

The instrument is set up to go through the following steps. Initial Gauge Length is calculated from the Initial Gauge Circumference which is determined during the Whole Article Force Test using separate identical articles, as described above. The Initial Gauge Length is defined as 50% of the Initial Gauge Circumference. The Final Gauge Length is calculated from the Full Circumference which is determined during the Whole Article Force Test, as described above.

| Crosshead Speed | 254.0 mm/min |
| Data Acquisition Rate | 50 Hz |
| Final Gauge Length | 0.5 × Full Circumference |
| Hold Time | 0 |
| Number of Cycles | 1 |

One end of the specimen is clamped into the upper clamp using the side seam area and the load is tared. The other end of the specimen is clamped into the lower clamp also using the side seam area, such that only the side seam areas are behind the contact line of the grip. The test is started and the specimen is extended to the Final Gauge Length at a crosshead speed of 254 mm/min, then immediately returned to the Initial Gauge Length at the same speed. The specimen is extended in the article transverse direction during the test. The unload force at 70% of the Final Gauge Length during the unload segments of the test is recorded.

Five articles are analyzed and the unload forces are recorded for each of the front and back zones 102, 104, 106, 108. The average tensile force (N) is calculated to the nearest 0.01 N for each zone including the front and back specimens for that zone. The tensile stress for each zone is calculated by the average tensile force (N) divided by the average longitudinal length (m) and reported to the nearest 0.1 N/m.

6. Belt Seam Shape Measurement

The Belt Seam Shape Measurement herein is for articles wherein the front belt and the back belt form a ring-like elastic belt, and all of the elastic bodies sandwiched between the inner sheet and the outer sheet run in the transverse direction substantially parallel to each other.

A belt specimen from the sample article and a board (hereinafter "stretch board") for supporting the specimen according to the size of the specimen are prepared.

The belt specimen is prepared by removing the waist belt 40 from the central chassis 38 of the article by separating the bonding between the waist belt and central chassis. Cold spray may be used, paying attention not to make wrinkles in the belt sections. Care is taken not to spray on any belt elastic body 96. The seam length LS (see FIG. 4, for example, wherein LS equals LF) of the sample is measured to within±1 mm with the belt laid flat and no tension applied.

The Full Circumference is determined during the Whole Article Force Test using separate identical articles as described above. The Full Stretch Width is defined as 50% of the Full Circumference.

Figure 9:
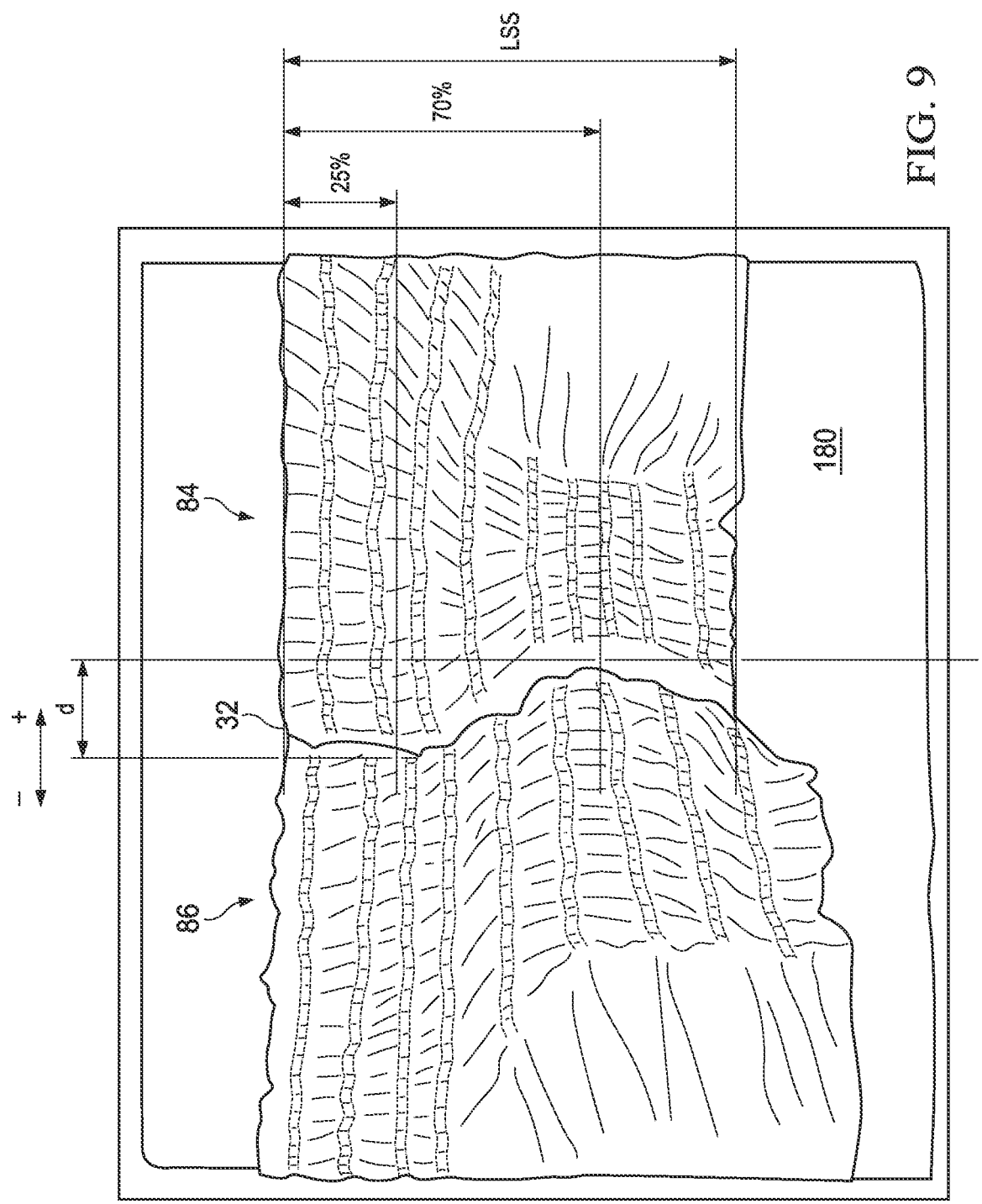
FIG. 9 is a side view of one embodiment of a wearable article of the present invention worn on a stretch board according to the "Belt Seam Shape Measurement".

Referring to FIG. 9, the stretch board 180 is made of polymethyl methacrylate, polycarbonate, or similar rigid material and has a dimension as such:

| Thickness | 8.5 mm ± 5 mm |
| Length | Between [the seam length (LS) + 40 mm] to [the seam length (LS) + 100 mm] |
| Width | 70% of the Full Stretch Width of the sample specimen − board thickness |

For example, if the belt side seam length LS is 130 mm, the stretch board length should be 170-230 mm. If the Full Stretch Width of the specimen is 355 mm and the board thickness is 8.5 mm, the board width should be 240 mm The stretch board 180 is inserted in the specimen while stretching the specimen as little as possible to insert the board, and in a manner such that the entire length of the seams 32 are placed on the front and back planes (and not on the sides) of the stretch board 180, such as shown in FIG. 10. The specimen is adjusted on the stretch board 180 so that the distal edge 88 (i.e. at the waist opening) of each seam 32 on one side and the other of the stretch board 180, as well as the proximal edge (i.e. at the leg opening) of each seam 32 on one side and the other of the stretch board 180 are aligned to within±5 mm, respectively, of the same longitudinal axis.

The specimen with the stretch board 180 inserted is then stood for 1 min to reach equilibrium in an environment at 25±2° C. and 50±10% relative humidity. Referring to FIG. 10, the linear end-to-end side seam length (rather than the contour length) in this stretched condition (LSS) is measured. The positions of the seam 32 in the transverse direction at points 70% of LSS away from the waist opening (70% point) and at 25% of LSS away from the waist opening (25% point) in the longitudinal direction are measured, and the difference "d" (unit: mm) is obtained. The value d is positive when the 70% point is located closer to the front longitudinal centerline of the belt compared to the 25% point. The value d is negative when the 25% point is located closer to the front longitudinal centerline of the belt compared to the 70% point. The d value is obtained for both seams 32 on either side of the stretch board 180. The "d" values are measured for five samples and the average d value (average of 10 values) is reported to the nearest 1 mm.

7. Scanning Electron Microscope (SEM) and Fourier Transform Infrared Spectroscopy (FTIR) Tests 7-1. Sample Preparation To obtain a nonwoven raw material sample, lay the material flat on a bench with the technical face-side upward, and a 20 mm (along machine direction) by 20 mm (in the perpendicular direction of machine direction) square shape of sample are cut using scissor. The technical face-side is the surface intended to be used as the garment-facing surface for the outer sheet 92 or the outer cover layer 42, and the body-facing surface for the inner sheet 94.

To obtain a sample from a finished article, the outer sheet 92 and inner sheet 94 is separated from the other components such as belt laminated nonwoven layers, or back sheet film by techniques such as applying "Quik-Freeze®" type cold spray, or other suitable methods that do not permanently alter the properties of the nonwoven composition. The technical face-side is the surface used as the garment-facing surface for the outer sheet 92 or the outer cover layer 42. The area where the elasticity of the belt elastic region is deactivated is preferred. A 20 mm by 20 mm square shape is cut out using scissors for obtaining the sample. For those articles having deactivated areas in the elastic belt region that are smaller than 20 mm by 20 mm, a 20 mm by 20 mm square shape is cut out using scissors, and the elastics are separated from the samples by techniques such as applying "Quik-Freeze®" type cold spray, or other suitable methods that do not permanently alter the properties of the nonwoven composition. Five samples are cut from the same portion of finished products from the same package for measurement.

7-2. Scanning Electron Microscope (SEM)

Scanning Electron Microscope images are taken using Hitachi TM3000 Bench-top SEM running Hitachi 3D-viewer software, or equivalent instrument. The 20 mm by 20 mm sample is submerged in liquid nitrogen and an edge is fractured with a razor blade (stainless steel coated, single edge industrial blades, 62-0165). Fractured samples are adhered to SEM mounts using double-sided Cu tape. The samples are sputter Au coated and are viewed in the SEM. The SEM images are acquired from top view, and x-section view. Fiber diameter and width measurements are made using the manual line tool in SEM operating software.

7-3. Fourier Transform Infrared Spectroscopy (FTIR)

Based on the SEM images described above, the structure of the material is observed. For samples made of monocomponent fibers, all measurements are conducted by FTIR-ATR under the following conditions. A small piece (enough to cover ATR crystal) of the sample is enough to do the measurement. Apply proper and consistent pressure on top of samples using ATR pressure arm.

| Instrument | PerkinElmer Spotlight 400 Fourier Transform Infrared Spectroscopy, or equivalent instrument |
|---|---|
| Collection mode | ATR-FTIR |
| Wavenumber range | 4000-600 cm$^{-1}$ |
| Accumulation | 16 scan |
| Spectral resolution | 4 cm$^{-1}$ |

For samples made of mixed fibers or multi-component fibers such as sheath-core, side-by-side structures etc, with the aim to understand each type of fiber in the mixed fiber or each distinct part of the multi-component fiber, a few fibers are separated from each sample under the stereoscope, and are squashed up by diamond cell to be measured by Micro-IR under the following conditions. Material identification is conducted using KnowItAll informatics system, or other reference spectra library.

| Instrument | Nicolet iN10, or equivalent instrument |
|---|---|
| Wavenumber range | 4000 to 700 cm$^{-1}$ |
| Accumulation | 64 scan |
| Spectral resolution | 4 cm$^{-1}$ |

EXAMPLES

Examples 1 and Examples A-G having the structure of a pant type wearable article are obtained and subject to measurements as described above.

Example 1

A Size 4 belt-type pant article having the configuration of FIGS. 2, 4, and elastic profiles of Table 1 below, with the outer sheet and outer cover layer made by tradename FJ206 available from Dayuan, Beijing China (20 gsm air-through carded nonwoven with 15 μm diameter PE/PET bicomponent fiber) and the inner sheet made by tradename HY15015-MALAYSIA-V2 available from Fibertex (15 gsm PP spunbond nonwoven).

Example A

A Size 4 belt-type pant article having the same configuration as Example 1 except the outer sheet made by dual 17 gsm PE/PP bicomponent spunbond nonwoven available from Fibertex, and the outer cover layer made by 25 gsm PP spunbond nonwoven with melt additive, available from Pegas.

Example B

A Size 4 uni-body type pant article sold by the tradename of "Merries Pants" purchased in Japan during October to December 2016 having Lot #20160404U0710956.

Example C

A Size 4 uni-body type pant article sold by the tradename of "Merries Pants" purchased in the Peoples Republic of China during October to December 2015 having Lot #20150124EOC30245.

Example D

A Size 4 belt-type pant article sold by the tradename of "Anerle Gold Pants" purchased in the Peoples Republic of China during October to December 2015 having Lot #WP014513603642.

Example E

A Size 4 uni-body type pant article sold by the tradename of "GooN Premium Pants" purchased in the Peoples Republic of China during October to December 2016 having Lot #20160614CA114400519, 27.

Example F

A Size 4 uni-body type pant article sold by the tradename of "Huggies Platinum Pants" purchased in the Peoples Republic of China during October to December 2016 having Lot #20160912 ND33 B.

Example G

A Size 4 belt-type pant article sold by the tradename of "Moony Pants" purchased in the Peoples Republic of China during October to December 2015 having Lot #201507243102.

TABLE 1

| | dtex/elongation %/number of elastic bodies |
|---|---|
| Front waist zone | 540 dtex/150%/4 |
| Front distal tummy zone | 540 dtex/150%/2 |
| | 540 dtex/150%/2 tummy cut |
| Front proximal tummy zone | 940 dtex/210%/8 tummy cut |
| Front leg zone | 540 dtex/150%/2 tummy cut |
| Back waist zone | 540 dtex/150%/4 |
| Back distal tummy zone | 940 dtex/130%/4 |
| Back proximal tummy zone | 540 dtex/210%/2 |
| | 540 dtex/210%/4 tummy cut |
| Back leg zone | 540 dtex/210%/2 tummy cut |

(*1) tummy cut in Table 1 refers to removal of elasticity at the central area of elastic strands which overlap the central chassis 38, resulting in 66% effective length of elasticity.

TABLE 2

| Example | Compression Work Index (gfcm) | Drapability Index (%) | Full circumference (mm) | Stretch circumference force (N) | Fit circumference force (N) |
|---|---|---|---|---|---|
| 1 | 77 | 9 | 663 | 6.4 | 2.8 |
| A | 60 | 9 | 690 | 4.5 | 2.2 |
| B | 110 | 27 | 662 | 7.3 | 3.9 |
| C | 116 | 29 | 661 | 7.3 | 3.8 |
| D | 81 | 14 | 636 | 7.5 | 3.9 |
| E | 89 | 20 | 644 | 8.0 | 4.6 |
| F | 92 | 23 | 622 | 8.9 | 3.7 |
| G | 92 | 14 | 618 | 8.7 | 4.0 |

Consumer Acceptance Test 30 panelists who are caregivers of babies using Size 4 pants diapers at a frequency of minimum 3 pads per day, and having a mixture of usage experience of major brands: "Merries", "Huggies Gold" and "Pampers"; were recruited. Each panelist was given 9 test products altogether on a table. Among the 9 test products, Examples 1, A, C, and D were included. The panelists were asked to sort the 9 products on to the scale 1-10 on the table for each question. The rating score of 30 panelists were averaged for the report as in Table 3. (The remainder of the 9 products except Examples 1, A, C, and D were those not listed in the Examples list above, and were; "Huggies Gold Pants", "Huggies Silver Pants", "Mammy Poko Pants", "Anerle Silver Pants", and "Goon Pants", all purchased in the Peoples Republic of China during October to November 2015.)

TABLE 3

| Values/Questions | 1 | A | C | D |
|---|---|---|---|---|
| Overall liking | 8.3 | 6.7 | 8.4 | 7.4 |
| Being soft | 8.9 | 8.0 | 8.0 | 7.6 |
| Underwear like | 8.4 | 5 | 7.9 | 7.5 |

Inventive Example 1 which meets the parametric requirements of the present invention have high acceptance for "overall liking" and highest acceptance of "underwear like" and "being soft" while the other examples which do not meet the parametric requirements of the present invention are slightly to significantly inferior in consumer acceptance in at least some aspect. The parameters of the present invention provide a good predictability of consumer acceptance in view of tactile and aesthetic sense provided by the article.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" Further, every numerical range given throughout this specification includes every narrower numerical range that falls within such broader numerical range.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wearable article continuous in a longitudinal direction and a transverse direction, comprising:
    an elastic belt region, a crotch region, a waist opening and two leg openings;
    wherein the elastic belt region is a laminate comprising an inner sheet made of nonwoven fiber, and an outer sheet made of nonwoven fiber, and a plurality of elastic bodies configured to stretch the elastic belt region in the transverse direction;
    wherein the elastic belt region is formed into an ring-like elastic belt comprising a front belt and a back belt, a center of the front belt is joined to a front waist panel of a central chassis, a center of the back belt is joined to a back waist panel of the central chassis, the front and back belt each having a left side panel and a right side panel where the central chassis does not overlap, wherein all of the elastic bodies sandwiched between the inner sheet and the outer sheet run in the transverse direction substantially parallel to each other;

wherein an entirety of a length of a belt side edge of the front belt is seamed with a certain length of a belt side edge of the back belt to define a seam length LS;

wherein the front belt and the back belt are each divided into 4 zones extending in the transverse direction and defined by its location from a distal edge to a proximal edge relative to a percentage of the seam length LS wherein; 0-25% is a waist zone, 25-50% is a distal tummy zone, 50-85% is a proximal tummy zone, and 85-100% is a leg zone; and wherein a tensile stress of the proximal tummy zone of the front belt is higher than a tensile stress of any other zone and no less than 200% of a tensile stress of the distal tummy zone of the front belt.

2. The article of claim 1, wherein a Drapability index is less than 25% according to the measurements herein.

3. The article of claim 1, wherein a Fit Circumference Force is more than 2N according to the measurements herein.

4. The article of claim 1, wherein the outer sheet has a material thickness of at least 0.25 mm at 500 Pa.

5. The article of claim 1, wherein the crotch region comprises an outer cover layer at a most garment facing side, and the outer cover layer is the same material as the outer sheet.

6. The article of claim 1, wherein each of the elastic bodies on the proximal tummy zone of the front belt are disposed at an elongation of from 150% to 250%.

7. The article of claim 1, wherein each of the elastic bodies disposed on the proximal tummy zone of the front belt has a density of no less than 540 dtex.

8. The article of claim 1, wherein a d value according to a Belt Seam Shape Measurement herein is no less than +10 mm.

9. The article of claim 1, wherein the front belt and the back belt each comprise the inner sheet, the outer sheet, and an outer sheet fold over; the front belt and the back belt each comprise transversely continuous proximal and distal edges, wherein the outer sheet fold over is an extension of the outer sheet formed by folding the outer sheet at the distal edge of the front belt and the back belt.

10. The article of claim 9, wherein the front belt comprises straight and transversely running proximal and distal edges, the front belt has a longitudinal length of LF; and the back belt comprises straight and transversely running proximal and distal edges, wherein the outer sheet fold over of the front belt has a longitudinal length of at least 0.3LF.

11. The article of claim 1, wherein the central chassis comprises an outer cover layer at a most garment facing side and a backsheet attached to a wearer facing surface of the outer cover layer; wherein a longitudinal length of the outer cover layer is longer than a longitudinal length of the crotch region and shorter than a longitudinal length of the backsheet, an area on the front waist panel or the back waist panel where the outer cover layer is present forms a transitional region, wherein a longitudinal length of the transitional region is no more than 10 mm.

* * * * *